US006416769B1

(12) United States Patent
Vromen

(10) Patent No.: US 6,416,769 B1
(45) Date of Patent: Jul. 9, 2002

(54) COSMETIC COMPOSITIONS COMPRISING EXFOLIATING ENZYMES AND USES THEREOF

(75) Inventor: Jacob Vromen, Botany (AU)

(73) Assignee: Australian Importers, Ltd., NV (US)

( * ) Notice: Subject to any disclaimer, the term of this patent is extended or adjusted under 35 U.S.C. 154(b) by 0 days.

(21) Appl. No.: 09/518,585

(22) Filed: Mar. 3, 2000

(51) Int. Cl.$^7$ .............................. A61K 7/00; A61K 7/04; A61K 38/48; A61K 39/385; A61K 9/14; A61F 13/02

(52) U.S. Cl. ...................... 424/401; 424/61; 424/94.63; 424/195.1; 424/448; 424/487; 514/54

(58) Field of Search ......................... 514/54; 424/195.1, 424/61, 94.63, 448, 487, 401

(56) References Cited

U.S. PATENT DOCUMENTS

| | | | | |
|---|---|---|---|---|
| 3,650,901 A | * | 3/1972 | Katchalski et al. | 195/63 |
| 4,556,554 A | * | 12/1985 | Calvo | 424/70 |
| 5,296,222 A | * | 3/1994 | Petersen et al. | 424/94.63 |
| 5,441,740 A | * | 8/1995 | Ozlen | 424/401 |
| 5,571,516 A | * | 11/1996 | Tezuka et al. | 424/401 |
| 5,578,312 A | * | 11/1996 | Parrinello | 424/401 |
| 5,665,366 A | * | 9/1997 | Rawlings et al. | 424/401 |
| 5,756,099 A | * | 5/1998 | Simpson | 424/195.1 |
| 5,976,556 A | * | 11/1999 | Norton et al. | 424/401 |
| 6,165,509 A | * | 12/2000 | Hoffman et al. | 424/487 |

OTHER PUBLICATIONS

Maioriello et al, "Immobilized protelytic enzymes as replacements for AHAs", Journal of the Society of Cosmetic Chemists, vol. 47, issue 4, 1997, pp. 289–292.*
Australian Importers, Ltd. invoice dated Jul. 29, 1998.
Confidentiality, Non–disclosure and Non–Use Agreement dated Jun. 17, 1998.
Medical Advisory Agreement, (dated Mar. 1, 1998).
Letter dated Apr. 23, 1999, from Ronald G. Wheeland, M.D., to Mr. Scott Shapiro.
Letter dated Mar. 1, 1999, from Ronald G. Wheeland, M.D., to Mr. Scott Shapiro.
Facsimile memo dated Aug. 24, 1998, from Scott Shapiro to Ronald L. Moy, M.D.
Letter dated Jun. 26, 1998 from Ronald L. Moy, M.D., to Scott Shapiro.
Letter dated Jun. 29, 1998 from Mark G. Rubin to Scott.
Clear Solutions Biotech, Inc. "Linked–Papain™ An Enzyme Alternative to AHA's" from website www.collabo.com/linkpap.htm, pp. 1–5, Sep. 5, 2001.
Katiyar et al., "Green Tea and Skin," *PubMed* (National Library of Medicine) *Arch Dermatol* Aug. 2000; 136(8):989–94, abstract only.
Zhao et al., "Green Tea Protects Against Psoralen Plus Ultraviolet A–Induced Photochemical Damages to Skin," *The Journal of Investigative Dermatology* 113, 1070–1075 (1999), abstract only.
Katiyar et al., "Green Tea Polyphenol Treatment to Human Skin Prevents Formation of Ultraviolet Light B–Induced Pyrimidine Dimers in DNA," *PubMed* National Library of Medicine) *Clin Cancer Res* Oct.; 2000 6(10):3864–9, abstract only.
Elmets et al., "Cutaneous Photoprotection From Ultraviolet Injury by Green Tea Polphenols," *PubMed* (National Library of Medicine) *J. Am Acad Dermatol* Mar. 2001; 44(3):425–32, abstract only.
Katiyar et al., "Green Tea Polyphenolic Antioxidants and Skin Photoprotection (Review)," *PubMed* (National Library of Medicine) *Int J Oncol* Jun. 2001; 18(6):1307–13, abstract only.

* cited by examiner

*Primary Examiner*—Michael G. Hartley
*Assistant Examiner*—Michael A. Willis
(74) *Attorney, Agent, or Firm*—Law Offices of Wayne A. Keown

(57) ABSTRACT

Cosmetic compositions for topical use that comprise an exfoliating enzyme for use in removal of at least a portion of the dead skin cells from the outer layer of skin, in conjunction with one or more botanicals, the delivery of which to subsurface layers and cells thereof of the skin is enhanced by the presence of the exfoliating enzyme. These compositions, including gels, lotions, and creams, are gentle, non-irritating and enhance the penetration of biological additives into the subsurface skin layers relative to currently commercially available compositions.

20 Claims, No Drawings

COSMETIC COMPOSITIONS COMPRISING EXFOLIATING ENZYMES AND USES THEREOF

BACKGROUND OF THE INVENTION

1. Field of the Invention

The present invention relates to cosmetic compositions comprising proteolytic enzymes which remove the stratum corneum of the skin, thus enhancing the penetration of other active components, including biological components, into the underlying layers of the skin.

2. Description of the Related Art

Exfoliants are compounds which remove the dead cell layer (stratum corneum) of the skin, and are used, for example, in the treatment of aging skin (removal of wrinkles), photodamaged skin, acne, dry skin, and other skin conditions. Currently commercially available cosmetic formulations for topical use typically include the following exfoliants: alpha hydroxy acids (AHAs) (e.g. glycolic acid and lactic acid), beta hydroxy acids (BHAs) and retinoids, which may cause adverse reactions including skin irritation, erythema, blistering, particularly in individuals with sun damaged skin, and chronic or unusually high photosensitivity, especially among ethnic groups having darker skin tones.

Thus, there is a need for cosmetic preparations comprising exfoliants which are effective and non-irritating, especially in individuals with sun damaged skin. The present invention addresses this need.

SUMMARY OF THE INVENTION

Performed embodiments of the present invention provide compositions for topical use, including but not limited to lotions, gels and creams, comprising an enzyme in combination with at least one, at least two, at least three or more, biological additive. Said enzyme is preferably papain, derivable from papaya, and is capable of removing the stratum corneum when applied thereto. The biological additives are preferably selected from the group consisting of *Echinacea angustifolia* extract, *mimosa tenuiflora* extract, *hydrocotyl* (*centella asiatica*) extract, *gingko biloba* extract, tea tree oil, *Matricaria chamomila* (*chamomile*) extract, *Hypericum perforatum* extract, and *Aloe barbedensis* extract, catemdiele extract, but may be any biologically-active biologic. The pH of the compositions described herein are preferably greater than about 4.5 or, more preferably, greater than 5.0, and are most preferably about 7.0.

Also described is a method for enhancing penetration of at least one, two three, or more biological additive into the skin, comprising applying to said skin a formulation comprising said at least one biological additive and an enzyme capable of removing at least a portion of the stratum corneum. The enzyme is preferably papain, is more preferably papain linked to a high molecular weight polymer, and is preferably papain linked to high molecular weight polyacrylic acid. Also provided is a method for treating an individual having skin exhibiting at least one condition selected from the group consisting of aging skin, photodamaged skin, acne, and dry skin, comprising: diagnosing a individual having said skin, applying to said skin a formulation comprising said at least one biological additive and an enzyme capable of removing at least a portion of the stratum corneum.

DETAILED DESCRIPTION OF THE PREFERRED EMBODIMENT

Preferred embodiments of the present invention provide effective, non-irritating topical cosmetic formulations comprising an enzyme which promotes removal of at least a portion of the stratum corneum of skin and therefore promotes deeper penetration of other compounds contained within the composition into subsurface skin. Thus, such an enzyme acts as an exfoliant, removing only portions of the dead cell layer of the skin, causing no damage to the underlying living cell layers. Currently available exfoliants, including AHAs, BHAs and retinoids tend to cause adverse topical reactions including but not limited to skin irritation, erythema and blistering. The topical enzymatic compositions disclosed herein have a pH that is more basic than the pH of skin, and preferably have a pH of about 7.0, thus contributing to their non-irritating properties relative to currently commercially available exfoliants.

One preferred enzyme is papain, an enzyme obtained from unripe papaya. One particularly preferred form of papain is Linked-Papain™ (papain carbomer, as described in CTFA, the International Cosmetic Ingredients Dictionary) in which papain is covalently immobilized to 1% polyacrylic acid (900,000 daltons), commercially available from Collaborative Laboratories, 3 Technology Drive, East Setauket, N.Y. 11733). In a preferred embodiment, the enzyme is present in the formulation in an amount between about 1% and 6%, more preferably between about 2% and 5%, most preferably about 4% by weight. The ability of papain to act as an exfoliant allows enhancement of penetration of any desired medicinal agent beneficial to the skin, such as, for example, biological additives (e.g, botanicals and herbals) and moisturizers. The activity of papain is greatest at a pH of 6, although the enzyme retains about 75% of its activity between pH 5 and 7. The cosmetic compositions preferably have a pH that is basic relative to the pH of skin (the pH of which typically ranging from approximately 4.5 to approximately 5.0), and preferably have a pH of about 7.0.

The papain compositions described herein may be formulated for topical application with pharmaceutically acceptable carriers using methods well known in the cosmetic and pharmaceutical arts, including gels, creams, ointments, emulsions, dispersions, salves, pastes, lotions and the like. These formulations may additionally comprise one or more emulsifiers, humectants (e.g., glycerin or glycerol, sorbitol, and the other known polyols), skin conditioning agents (e.g., propylene glycol, sweet almond oil, apricot kernel oil), surfactants (e.g. ceteth-20), colorants such as staining dyes and pigments (e.g, calcium, barium and aluminum lakes, iron oxides, titanium dioxide and mica), antioxidants (i.e., ascorbic acid, tocopherols, ascorbyl palmitate, thiodipropionic acid), viscosity-enhancing agents (e.g., cetearyl alcohol, polyethylene glycol), vitamins, minerals, emollients, skin conditioning agents, biological additives (e.g. botanicals or herbals), sunscreens (e.g. octyl methoxycinnamate, butyl methoxydibenzolylmethane, oxybenzone), pH adjusters, solvents, germicides (e.g., antibiotics, Tricolsan), preservatives (e.g., BHT, methylparaben, ethylparaben, propylparaben, butylparaben) and fragrances (e.g., strawberry extract, *mangifera indica*). It will be appreciated by those of skill in the art that particular compounds may be properly classified in one, or two or more of the above-listed classifications of compound types.

The compositions may also include one or more biological additives, such as botanicals or herbals. As used herein, the term "biological additive" indicates any compound obtained from a natural source, including plants, animals, bacteria and yeast, which has a medicinal or otherwise beneficial effect when topically applied to the skin. Examples of biological additives include oil of *Melaleuca* alternifolia, oil of *Lavandula angustifolia, Carica papaya* extract, *Echinacea angustifolia* extract, *Mimosa tenuiflora* extract, *Hydrocotyl (centella) asiatica* extract, *gingko biloba* extract, oil of *Melaleuca alternifolia* (tea tree oil), *Matricaria chamomila* (chamomile) extract, *Hypericum perforatum* extract, *Aloe barbedensis* extract, and the like. The biological sources for "biological additive" may also include, but are not limited to the following: Aloe Vera, *Aloe Barbedensis*; Arnica, *Arnica Montana*; Bladderwrack (seaweed), *Fucus Vesciculosis*; Birch, *Betula Alba (Pendula)*; Chamomile, *Matricaria Chamomila (Chamomila Recutita)*; Marsh Mallow, *Althea Officinalis;* Meadow Sweet, *Spirea Ulmaria (Filipendula)*; Mint/Lemon Balm, *Melissa Officinalis*; Mimosa, *Mimosa Tenuiflora; Myrrh Tincture, Commiphor Myrrha*; Neem, *Melia Azadirachta*; Nettle (stinging), *Urtica Dioica*; Papaya, *Carica Papaya*; Propolis (bee glue), *Propolis Cera*; Raspberry, *Rubis Idaeus; Red Poppy, Papaver Rhoeas; Rose Hip* (dog rose), *Rosa Carima*; Rosemary, *Rosemarinus Officinalis*; Sage, *Salvia Officinalis*; St. Johns Wort, *Hypericum Perforatum*; Strawberry, *Fragaria Vesca; Thea Sinensis* (green tea), *Camelia Sinensis*; Walnut, *Juglans Regia*; Witchhazel (dist/extr), *Hamamelis Virginiana*; Yarrow, *Achillea Millefolium*; Wild Yam, *Dioscorea Villosa;* Hawthorn, *Crataegus Monogina/Oxyantha*; Herma (black/rod), *Lawsoma Ehemus*; Hops, *Humulus Lupulus*; Horse Chestnut, *Aesculus Hippocastanum;* Horse Tail, *Equisitum Arvense*; Ivy, *Hedera Helix; Linden/Lime* Tree Blossoms, *Tilia Argentea Cordata*; Madder, *Rubia Tinctorum*; Marigold, *Calendula Officinalis; Centella Asiatica, Centella Asiatica Urban (hydrocotyl Asiatica)*; Carrot (roots), *Daucus Carota*; Comfrey (Allantoine), *Symphytum Officinale*; Coneflower (Echinacea), *Echinacea Angustifolia*; Cucumber, *Cucumis Sativus (Frucus Cucumis)*; Fenugreek, *Trigonella Foenum Greacum*; Gingko, *Gingko Biloba*; Ginseng, *Panax Ginseng*; Great Burdock, *Radix Bardanea/Arctium Lappa*; Tea Tree Oil, Oil of *Melaleuca Alternifolia*; Colts Foot, *Tussilago Farfara*; Clover, *Trifolium Pratense*; Speedwell, *Veronica Officinalis.*

Further biological additives, along with the biological or medicinal properties of the biological additives described herein and of other known biological additives are know to those of skill in the art. References, including encyclopedias and treatises, known to those of skill in the art, that described such biological additives, along with the biological or medicinal properties of the biological additives described herein, include: Guenther—The Essential Oils, Van Nostrand; Int. Cosmetic Ingredient Dictionary, Vol 1 & 2, C.T.F.A. 1995; Int. Cosmetic Ingredient Handbook, C.T.F.A. 1995; British Herbal Pharmacopoeia, British Herbal Medicine Assoc., 1983; Clinical Applications of Ayurvedic & Chinese Herbs, K. Bone, Phytotherapy Press, 1996; A Handbook of Chinese Healing Herbs, D. Reed, Shambala, Boston, 1995; Echinacea—Nature's Immune Enhancer, S. Foster, Healing Arts Press, Rochester, 1991; Encyclopedia of Herbs, D. Brown, RD Press, 1995; Encyclopedia of Medicinal Plants, A. Chevalier, Dorling Kingers Ley, 1996; L'Angelica—Herbal Extracts; Cosmetochem—Herbasol Extracts. These references are incorporated herein in their entirety.

Emulsifiers contemplated for use include but are not limited to monoacyl glycerol, such as glyceryl monoalkanoates, glyceryl monoalkenoates, diacyl 1,2- or 1,3-disubstituted) glycerol, such as glyceryl dialkanoates, glyceryl dialkenoates, polyglyceryl esters, stearic acid, cetyl alcohol, and sorbitan stearate.

Other examples of biological additives include, but are not limited to, *Carica papaya* extract, *Echinacea angustifolia* extract, tea tree oil, *Mimosa tenuiflora* extract, *Hydrocotyl (centella asiatica)* extract, *gingko biloba* extract, *Matricaria chamomila* (chamomile) extract, *Hypericum perforatum* extract, *Aloe barbedensis* extract, and the like. A particularly preferred biological additive is *tea tree oil*. In a preferred embodiment, one or more biological additives is present in the formulation in a combined amount of from about 1% to 10% by weight, more preferably from about 2% to 8% by weight, and most preferably from about 4% to 6% by weight.

In a preferred embodiment, one or more skin conditioning agent(s) is present in the formulation in a combined amount of from about 1% to 20% by weight, more preferably from about 5% to 10% by weight, and most preferably from about 6% to 9% by weight.

In another preferred embodiment, one or more emollients or humectants is present in the formulation in a combined amount of from about 1% to 10% by weight, more preferably about 2% to 8% by weight.

One or more viscosity increasing agents may be present in the formulations in an amount from about 2% to 10% by weight, preferably about 5% by weight.

One or more antioxidants may also be present in a combined amount of between about 0.1% and 5% by weight, preferably between about 0.5% and 2% by weight.

In another preferred embodiment, one or more emulsifying agents is present in a combined amount of between about 1% and 20% by weight, more preferably between about 5% and 10% by weight.

In another preferred embodiment, one or more antioxidants, preservatives and fragrances is present in the compositions in minor amounts, preferably between about 0.05% and 5% by weight, more preferably between about 0.1% and 2% by weight.

Preferably, the compositions and formulations are directly applied to the skin once per week, once per day, twice per day or three times per day. Alternatively, the compositions and formulations may be applied directly to the skin less frequently or only on specific occasions, for example after a sunburn when the skin is peeling, to achieve certain of the benefits described herein. The quantity and extent of application will vary with the particular result desired or condition to be treated. Such preferred application will vary from about 1 mg per $cm^2$ skin per day to 50 mg per $cm^2$ skin per day, massaged into the skin, as will be appreciated by those of skill in the art, depending on the severity and the condition to be treated.

EXAMPLES

The following three examples are illustrative, but not limiting, of topical papain formulations.

Example 1

A preferred moisturizing formulation contains:

Papain-containing moisturizer

| COMPOUND | APPROX. WEIGHT % | TYPE OF COMPOUND |
| --- | --- | --- |
| deionized water | 70.3 | solvent |
| stearic acid | 3.5 | emulsifier |
| cetyl and/or myristyl alcohol | 3.5 | emulsifier |

-continued

| COMPOUND | APPROX. WEIGHT % | TYPE OF COMPOUND |
|---|---|---|
| sweet almond oil | 3.5 | emollient |
| propylene glycol | 3.5 | humectant, solvent, skin conditioning agent |
| polysorbate-60 | 2.5 | emulsifier |
| safflower or sunflower oil | 2.5 | emollient, skin conditioning agent |
| jojoba oil | 2 | skin conditioning agent |
| octyl methoxycinnamate | 2 | ultraviolet light absorber |
| papain carbomer | 2 | exfoliant |
| carica papaya extract | 0.5 | biological additive |
| sorbitan stearate | 0.5 | emulsifier |
| tilia cordata (argentea) extr. | 0.5 | biological additive |
| echinacea angustifolia extr. | 0.5 | biological additive |
| mimosa tenuiflora extr. | 0.5 | biological additive |
| hydrocotyl (centella asiatica) extract | 0.5 | biological additive |
| aloe barbedensis extract | 0.25 | biological additive |
| matricaria chamomila extr. | 0.25 | biological additive |
| hypericum perforatum extr. | 0.25 | biological additive |
| tocopherol | 0.5 | antioxidant, skin conditioning agent |
| methyl/ethyl/propyl/butyl parabens in phenoxyethanol | 0.25 | preservative |
| Octhilinone | 0.1 | preservative |
| mangifera indica | 0.1 | fragrance |

Example 2

A preferred cream formulation of the present invention was prepared in the 5 following manner: (1) Cetyl and/or myristyl alcohol, stearic acid, polysorbate-60, sorbitan stearate, safflower (or sunflower) oil, jojoba oil, α-tocopherol, sweet almond oil and octylmethoxycinnamate were combined and melted at a temperature not exceeding 70° C. until homogeneous. (2) When molten, but not overheated, half of the deionized water (at approximately 70° C.) was added while mixing, resulting in formation of an emulsion. (3) The remaining deionized water (cold) was then added. (4) The emulsion was cooled to 40° C., followed by addition of propylene glycol, carica papaya extract, *tilia cordata* extract, *Echinacea angistifolia* extract, *Mimosa tenuiflora* extract, Centella (hydrocotyl) extract, *aloe barbedensis* (decolorized) extract, *Matricaria chamomila* extract, and *Hypericum perforatum* extract. (5) The emulsion was cooled to 35° C., followed by addition of octhilinone, parabens, papain carbomer and mangifera indica. If necessary, the emulsion is homogenized.

Example 3

A preferred lotion formulation contains:

| PAPAIN-CONTAINING LOTION | | |
|---|---|---|
| compound | weight % | type of compound |
| deionized water | 80 | solvent |
| cetyl or myristyl alcohol | 3 | emulsifier |
| paraffin liquid | 2.8 | skin conditioning agent, emollient |
| stearic acid | 2.6 | emulsifier |
| papain carbomer | 4.0 | exfoliant |
| carica papaya extract | 2 | biological additive |
| polysorbate-60 | 1.4 | emulsifier |
| propylene glycol | 4.0 | humectant, solvent, skin conditioning agent |

-continued

| PAPAIN-CONTAINING LOTION | | |
|---|---|---|
| compound | weight % | type of compound |
| sorbitan stearate | 0.4 | emulsifier |
| tilia cordata (argentea) extract | 0.6 | biological additive |
| echinacea augustifolia extr. | 0.6 | biological additive |
| aloe barbedensis extr. | 0.6 | biological additive |
| matricaria chamomila extr. | 0.6 | biological additive |
| calendula officinalis extr. | 0.6 | biological additive |
| hydrocotyl (centella asiatica) extract | 0.6 | biological additive |
| hypericum perforatum extr. | 0.4 | biological additive |
| methyl/ethyl/propyl/butyl parabens in phenoxyethanol | 0.3 | preservative |
| octhilinone (methylchloro-isothiazolinone and methyl-isothiazoline) | 0.1 | preservative |
| FD & C Red No. 3 & Yellow No. 5 | | colorant |
| mangifera indica | 0.2 | fragrance |

Example 4

A preferred lotion formulation of the present invention was prepared in the following manner: Cetyl or myristyl alcohol, stearic acid, polysorbate-60, sorbitan stearate, paraffin liquid and α-tocopherol were combined and melted at 70° C. until homogeneous. Half of the water was added hot (70° C.) and the mixture was mixed thoroughly, followed by addition of the remainder of the water (cold through room temperature; approximately 15° C.–18° C.). The mixture was cooled to 40° C., followed by addition of propylene glycol, *tilia cordata* extract, *Echinacea angustifolia* extract, *aloe barbedensis*-distilled extract (aloe vera clear), *Matricaria chamomila* extract, *Calendula officinalis* extract, *Centella (hydrocotyl) asiatica* extract, *Hypericum perforatum* extract. All extracts were diluted 1:5 in either propylene glycol or butylene glycol. When the mixture had cooled to 30–35° C., octhilinone, methyl/ethyl/propylibutyl parabens, colorants (to shade), *mangifera indica* and papain carbomer were added. If necessary, the mixture is homogenized.

Example 5

A preferred gel formulation contains:

| Papain-containing gel | | |
|---|---|---|
| Compound | weight % | type of compound |
| deionized water | 80 | solvent |
| carbomer | 0.9 | viscosity increasing agent |
| papain | 4 | exfoliant |
| propylene glycol | 4 | solvent |
| triethanolamine | 1 | pH adjuster |
| carica papaya extract | 2 | biological additive |
| betula alba extract | 1 | biological additive |
| cucumis staivus extr. | 1 | biological additive |
| panax ginseng extract | 1 | biological additive |
| aesculus hippocastanum extract | 1 | biological additive |
| tilia argentea cordata extr. | 0.1 | biological additive |
| propolis cera extract | 0.5 | biological additive |
| octhilinone | 0.1 | preservative |

Example 6

A preferred gel formulation of the present invention was prepared in the following manner: Carbomer was added to cold deionized water while mixing. When dispersed, propylene glycol, *carica papaya* extract, *betula alba* extract, *cucumis sativus* extract, *panax ginseng* extract, *aesculus hippocastanum* extract, *tilia argentea* extract and *propolis cera* extract were added. These ingredients were mixed well, followed by addition of papain carbomer (1–4%) and octhilinone, and thorough mixing. Deionized water and triethanolamine were then added slowly (to prevent introduction of air) to form the clear gel.

Although the foregoing invention has been described in some detail by way of illustration and example for purposes of clarity of understanding, it is readily apparent to those of ordinary skill in the art in light of the teachings of this invention that certain changes and modifications, particularly with regard to specific exemplary components and to the specific ranges of the components of the formulation, may be made thereto without departing from the spirit and scope of protection afforded the present invention described, and claimed, herein.

What is claimed is:

1. A composition for topical use comprising papain, *Echinacea angustifolia* extract, and *hydrocotyl* (*centella asiatica*) extract wherein the papain is present at least about 2%, by weight, in the composition.

2. The composition of claim 1, wherein the papain is present at about 2% to about 4%, by weight.

3. The composition of claim 2, wherein the papain is linked to a high molecular weight polymer via a covalent attachment or a non-covalent interaction.

4. The composition of claim 3, wherein the high molecular weight polymer is polyacrylic acid.

5. The composition of claim 1, further comprising a biological additive selected from the group consisting of *mimosa tenuiflora* extract, *gingko biloba* extract, *tea tree oil, green tea, Matricaria chamomila* (chamomile) extract, *Hypericum perforatum* extract, and *Aloe barbedensis* extract.

6. The composition of claim 1, wherein the pH of said composition is greater than about 4.5.

7. The composition of claim 1, wherein the pH of said composition is about 7.0.

8. A method for enhancing penetration of at least two biological additives into the skin, comprising applying to said skin a formulation comprising papain and at least two biological additives, wherein the biological additives are selected from the group consisting of *Echinacea angustifolia* extract, *hydrocotyl* (*centella asiatica*) extract and green tea, and wherein the papain is present at least about 2%, by weight, in the formulation.

9. The method of claim 8, wherein said papain is linked to a high molecular weight polymer via a covalent attachment or a non-covalent interaction.

10. The method of claim 9, wherein said high molecular weight polymer is polyacrylic acid.

11. The method of claim 8, wherein the method enhances the penetration of at least three biological additives into the skin.

12. A method for treating an individual having skin exhibiting at least one condition selected from the group consisting of wrinkling due to aging, photodamaged skin, acne, and dry skin, comprising:

applying to said skin a formulation comprising papain, *Echinacea angustifolia* extract and *hydrocotyl* (*centella asiatica*) extract wherein the papain is present at least about 2%, by weight, in the composition.

13. The method of claim 12, wherein the papain is linked to a high molecular weight polymer via a covalent attachment or non-covalent interaction.

14. The method of claim 13, wherein the high molecular weight polymer is polyacrylic acid.

15. The method of claim 12, wherein the condition is wrinkling due to aging.

16. The method of claim 12, wherein the condition is photodamaged skin.

17. The method of claim 12, wherein the condition is acne.

18. The method of claim 12, wherein the condition is dry skin.

19. The composition of claim 1, further comprising *green tea*.

20. The method of claim 12, Wherein the formulation further comprises green tea.

* * * * *